(12) United States Patent
Shindo et al.

(10) Patent No.: US 8,646,306 B2
(45) Date of Patent: Feb. 11, 2014

(54) METHOD FOR MANUFACTURING SENSOR ELEMENT FOR GAS SENSOR

(75) Inventors: Hiroyuki Shindo, Kasugai (JP); Kiyotaka Sugiura, Kani (JP)

(73) Assignees: NGK Insulators, Ltd., Nagoya (JP); NGK Ceramic Device Co., Ltd., Komaki (JP)

(*) Notice: Subject to any disclaimer, the term of this patent is extended or adjusted under 35 U.S.C. 154(b) by 558 days.

(21) Appl. No.: 12/945,119

(22) Filed: Nov. 12, 2010

(65) Prior Publication Data
US 2011/0138875 A1 Jun. 16, 2011

(30) Foreign Application Priority Data

Dec. 14, 2009 (JP) ................................ 2009-282789

(51) Int. Cl.
*G01N 27/419* (2006.01)
*G01R 3/00* (2006.01)
*H01L 21/66* (2006.01)
*H05K 3/12* (2006.01)
*G01N 27/407* (2006.01)
*G01N 27/416* (2006.01)

(52) U.S. Cl.
CPC ............ *H01L 22/14* (2013.01); *G01N 27/4071* (2013.01); *G01N 27/4074* (2013.01); *G01N 27/4163* (2013.01)
USPC ................................. 73/1.06; 29/593; 205/67

(58) Field of Classification Search
CPC .......... G01N 27/4071; G01N 27/4073; G01N 27/4074; G01N 27/4163; G01N 27/4166; G01N 27/4175; G01R 31/2829; G01R 31/2831; H01L 22/00; H01L 22/10; H01L 22/14; H01L 2021/70; H01L 2021/77

USPC ...................... 29/593; 73/1.06, 23.31; 205/67
See application file for complete search history.

(56) References Cited

U.S. PATENT DOCUMENTS 4,845,426 A * 7/1989 Nolan et al. .............. 324/750.03
5,210,041 A * 5/1993 Kobayashi et al. ..... H01L 21/66
(Continued)

FOREIGN PATENT DOCUMENTS

EP 1 582 865 A1 10/2005
EP 2 082 870 A2 7/2009
(Continued)

OTHER PUBLICATIONS

Japanese Office Action dated Jan. 29, 2013, in Japanese.
(Continued)

*Primary Examiner* — Thomas P Noland
(74) *Attorney, Agent, or Firm* — Burr & Brown, PLLC (57) ABSTRACT

A method for manufacturing a gas sensor element includes (a) printing a wiring pattern of a conductive paste on a green sheet for an oxygen-ion conductive solid electrolyte; (b) laminating a plurality of green sheets including the green sheet having been subjected to step (a) and integrating the plurality of green sheets; (c) cutting out a plurality of element bodies from the laminated body; (d) baking the element body cut out by step (c); (e) heating the element body having been subjected to step (d), in a reducing atmosphere; (f) driving the element body having been subjected to step (e), in an inspection-purpose gas atmosphere for a predetermined time period; and (g) inspecting electrical characteristics of the element body having been subjected to step (f). The element body having passed the inspection of step (g) is assembled as a sensor element in a gas sensor.

14 Claims, 7 Drawing Sheets

(56) References Cited

U.S. PATENT DOCUMENTS

| | | | |
|---|---|---|---|
| 5,821,435 A * | 10/1998 | Kojima | 73/863.01 |
| 5,902,469 A | 5/1999 | Kato et al. | |
| 6,057,694 A * | 5/2000 | Matsudo | H01L 21/66 |
| 6,721,649 B2 * | 4/2004 | Knott et al. | 73/23.31 X |
| 7,454,945 B1 * | 11/2008 | Kita et al. | 73/1.06 X |
| 2005/0218337 A1 * | 10/2005 | Kai et al. | 250/441.11 |
| 2008/0099334 A1 | 5/2008 | Yamauchi | |
| 2009/0188297 A1 * | 7/2009 | Willett et al. | 73/1.06 |
| 2009/0188620 A1 | 7/2009 | Okuda et al. | |
| 2009/0215180 A1 * | 8/2009 | Bos | 436/8 |
| 2011/0309850 A1 * | 12/2011 | Yoshida et al. | G01R 31/28 |

FOREIGN PATENT DOCUMENTS

| | | | |
|---|---|---|---|
| JP | 2009-175099 A1 | 8/1999 | |
| JP | 2000180410 A * | 6/2000 | G01N 27/416 |
| JP | 3537983 B2 | 3/2004 | |
| JP | 2004-294079 A1 | 10/2004 | |
| JP | 2006-284223 A1 | 10/2006 | |

OTHER PUBLICATIONS

Extended European search report for EP-10251939.4 dated Mar. 4, 2011.

* cited by examiner

METHOD FOR MANUFACTURING SENSOR ELEMENT FOR GAS SENSOR

BACKGROUND OF THE INVENTION

1. Field of the Invention

The present invention relates to a method for manufacturing a sensor element for a gas sensor, and particularly relates to a method for stabilizing an electrode state.

2. Description of Related Art

Conventionally, various gas sensors have been used for recognizing a concentration of a desired gas component in a measurement gas. For example, as a device for measuring a NOx concentration in a measurement gas such as a combustion gas, known is a NOx sensor having a sensor element which is formed using an oxygen-ion conductive solid electrolyte such as zirconia ($ZrO_2$) (for example, see Japanese Patent Application Laid-Open No. 2006-284223 and Japanese Patent No. 3537983).

In sensor elements of gas sensors including the NOx sensors disclosed in Japanese Patent Application Laid-Open No. 2006-284223 and Japanese Patent No. 3537983, a concentration of an object component in a measurement object gas is obtained by utilizing the fact that in a case where the measurement object gas component is decomposed at a measuring electrode, the amount of oxygen ion occurring at that time is proportional to a current flowing in the measuring electrode and a reference electrode. To be specific, a concentration value of the object component is recognized as follows: a relationship (sensitivity characteristics, a concentration profile) between a concentration value and a current value (output signal value) in each individual sensor element is obtained in advance by using a mixed gas whose object component concentration is already known; and in an actual use, a measured current value is converted into a concentration value based on the sensitivity characteristics.

Therefore, it is ideal that the current value is zero in a case where the object component does not exist in the measurement gas. However, actually, oxygen originally existing in the measurement gas is, though removed prior to the decomposition of the object gas component, left in a small amount and is decomposed, so that a current slightly flows. Accordingly, it is normal that prior to use, a current value (derived from residual oxygen and the like) under a state where the object component does not exist is identified as an offset value, and a value obtained by subtracting the offset value from a current value obtained under a state where the object component exists is used as a current value which is proportional to a gas concentration.

The above-described sensitivity characteristics are determined before each gas sensor is used (for example, before shipment), and normally dealt as fixed characteristics without being changed when the gas sensor is used afterward. This is based on the assumption that actual sensitivity characteristics do not vary during the use of the gas sensor. If the actual sensitivity characteristics change over time, the concentration value which is calculated based on the sensitivity characteristics determined at the time of shipment loses its reliability as the use of the gas sensor continues, and eventually the gas sensor loses a measurement accuracy set in its specification.

To ensure the measurement accuracy, in a manufacturing process of a sensor element, inspection of device characteristics is performed to evaluate electrical characteristics of a sensor element, and if sensitivity characteristics of a sensor element vary or do not satisfy a predetermined specification (management range), it is determined that the sensor element is a defective product.

For improvement of the yield of the product, it is necessary to reduce occurrence of the defective product. The inventors of the present invention have conducted intensive studies, and consequently found out that, for the reason of instability of an oxidation-reduction state in various electrodes provided within the sensor element, that is, the fact that the degree of oxidation at the time of baking an element and the degree of reduction caused by a subsequent aging process performed in a rich atmosphere are not constant, and for the reason that a rich component remaining within the aged sensor element is unexpectedly decomposed, an electrode state in the sensor element after the aging process is instable. And they also have found out the fact that the inspection of device characteristics and the determination of sensitivity characteristics have been conventionally performed under such an instable condition.

SUMMARY OF THE INVENTION

The present invention relates to a method for manufacturing a sensor element for a gas sensor, and particularly is directed to stabilization of a state of an electrode provided in the sensor element.

According to the present invention, a method for manufacturing a sensor element for a gas sensor is provided. The sensor element includes an electrochemical pumping cell and an electrochemical sensor cell. The method includes the steps of: (a) printing and forming a wiring pattern of a conductive paste on a green sheet containing, as a main component, ceramic which is an oxygen-ion conductive solid electrolyte; (b) laminating a plurality of green sheets including the green sheet having been subjected to the step (a), and integrating the plurality of green sheets; (c) cutting out a plurality of element bodies from a laminated body obtained by the step (b); (d) baking the element body cut out by the step (c); (e) heating the element body having been subjected to the step (d), in a reducing atmosphere; (f) driving the element body having been subjected to the step (e), in an inspection-purpose gas atmosphere for a predetermined time period; and (g) inspecting electrical characteristics of the element body having been subjected to the step (f). The element body having passed the inspection of the step (g) is assembled as the sensor element in a gas sensor.

According to the present invention, a state of electrodes included in the sensor element is stabilized, and in this condition the inspection of device characteristics is performed. This can prevent, in the inspection of device characteristics, occurrence of an erroneous decision which determines that a sensor element which should be determined to be a non-defective product is a defective product. Additionally, the sensitivity characteristics having reliability can be surely determined. Thus, the yield of the product can be improved, and a gas sensor having high reliability can be realized.

Preferably, a method for manufacturing a sensor element for a gas sensor according to the present invention further includes, between the step (f) and the step (g), the step of (h) leaving the element body having been subjected to the step (f), in the air. The element body having been subjected to the step (h) is inspected in the step (g).

Therefore, an object of the present invention is to provide a method for manufacturing a sensor element capable of improving the yield of the product and realizing a gas sensor having high reliability.

These and other objects, features, aspects and advantages of the present invention will become more apparent from the following detailed description of the present invention when taken in conjunction with the accompanying drawings.

DESCRIPTION OF THE PREFERRED EMBODIMENTS

Outline Structure of Sensor Element

Figure 1:
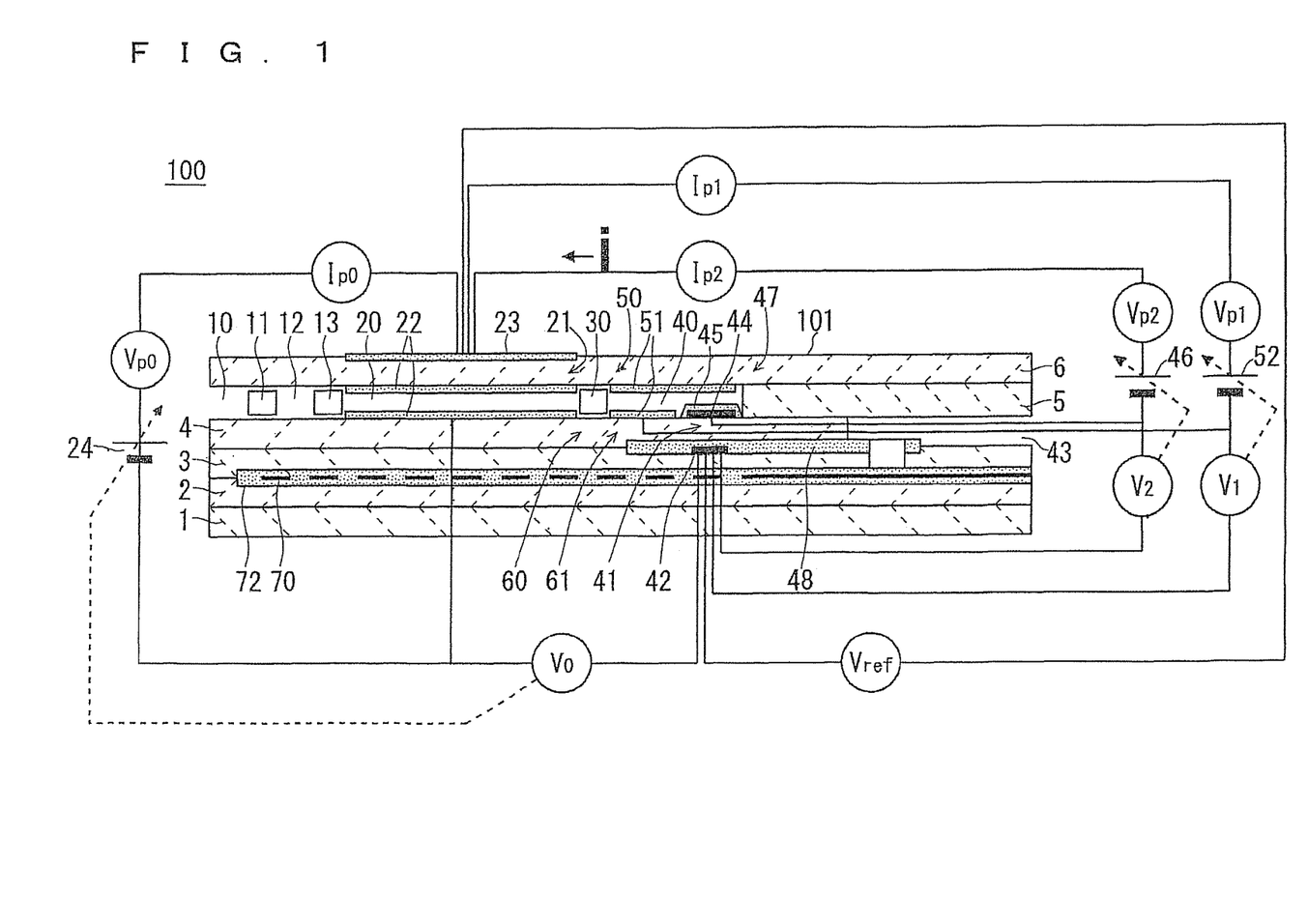
FIG. 1 is a cross-sectional view schematically showing a structure of a sensor element 101 included in a NOx sensor 100.

FIG. 1 is a cross-sectional view schematically showing a structure of a sensor element 101 included in a NOx sensor 100. A structural material of the sensor element 101 shown in FIG. 1 is ceramic containing, as a main component, zirconia which is an oxygen-ion conductive solid electrolyte.

More specifically, the sensor element 101 has a structure in which six layers, namely, a first substrate layer 1, a second substrate layer 2, a third substrate layer 3, a first solid electrolyte layer 4, a spacer layer 5, and a second solid electrolyte layer 6, are laminated in the mentioned order from the bottom side seen in FIG. 1, each of the layers being formed of an oxygen-ion conductive solid electrolyte.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are adjacently formed in the mentioned order so as to be in communication with one another. The gas inlet 10, the buffer space 12, the first internal space 20, and the second internal space 40 are spaces within the sensor element 101 provided by hollowing out the spacer layer 5, in which their upper portions are defined by the lower surface of the second solid electrolyte layer 6, their lower portions are defined by the upper surface of the first solid electrolyte layer 4, and their side portions are defined by a side surface of the spacer layer 5. Each of the first diffusion control part 11, the second diffusion control part 13, and the third diffusion control part 30 is provided as two horizontally long slits (whose openings are elongated in a direction perpendicular to the plane of the drawing sheet of FIG. 1). A part extending from the gas inlet 10 to the second internal space 40 is also referred to as a gas distribution part.

At a position which is farther from the end portion than the gas distribution part is, a reference gas inlet space 43 is provided between an upper surface of the third substrate layer 3 and a lower surface of the spacer layer 5. The reference gas inlet space 43 is a space within the sensor element 101, in which its upper portion is defined by the lower surface of the spacer layer 5, its lower portion is defined by the upper surface of the third substrate layer 3, and its side portion is defined by a side surface of the first solid electrolyte layer 4. A reference gas, for example, air, is introduced into the reference gas inlet space 43.

The gas inlet 10 is open to the outside, and a measurement gas is taken into the sensor element 101 from the outside through the gas inlet 10.

The first diffusion control part 11 applies a predetermined diffusion resistance to the measurement gas taken through the gas inlet 10.

The buffer space 12 is provided for canceling a concentration fluctuation of the measurement gas, which is caused by a pressure fluctuation of the measurement gas (a pulsation of exhaust gas pressure, in a case where the measurement gas is an automobile exhaust gas).

The second diffusion control part 13 applies a predetermined diffusion resistance to the measurement gas introduced from the buffer space 12 into the first internal space 20.

The first internal space 20 is provided as a space for adjusting oxygen partial pressure in the measurement gas introduced through the second diffusion control part 13. The oxygen partial pressure is adjusted by the operation of a main pumping cell 21.

The main pumping cell 21 is an electrochemical pumping cell constituted by an inside pump electrode 22, an outside pump electrode 23, and a part of the oxygen-ion conductive solid electrolyte interposed between these electrodes. The inside pump electrode 22 is provided at substantially entire parts of the lower surface of the second solid electrolyte layer 6 and the upper surface of the spacer layer 5 facing the first internal space 20. The outside pump electrode 23 is provided in a region on an upper surface of the second solid electrolyte layer 6 corresponding to the inside pump electrode 22, so as to be exposed to the outside. Each of the inside pump electrode 22 and the outside pump electrode 23 is foamed as a porous cermet electrode (for example, a cermet electrode including a noble metal containing 0.01 wt % to 0.95 wt % of Au and zirconia) having a rectangular shape in a plan view. The inside pump electrode 22 is formed using a material having a weakened reduction ability with respect to a NO component in the measurement gas, or having no reduction ability with respect to the NO component in the measurement gas. That is, the inside pump electrode 22 is provided as a pump electrode having a low NO-reducing property, in which the reducing property with respect to the NO component is suppressed.

In the main pumping cell 21, a pump voltage Vp0 is applied by a variable power source 24 provided in the outside of the sensor element 101, to make a pump current Ip0 flow in a positive direction or a negative direction between the outside pump electrode 23 and the inside pump electrode 22, and this allows oxygen existing within the first internal space 20 to be pumped out to the outside or oxygen existing in the outside to be pumped into the first internal space 20.

In the sensor element 101, a first oxygen-partial-pressure detection sensor cell 60 which is an electrochemical sensor cell is constituted by the inside pump electrode 22, a reference electrode 42, and a part of the oxygen-ion conductive solid electrolyte interposed between these electrodes. The reference electrode 42 is interposed between the upper surface of the third substrate layer 3 and the first solid electrolyte layer 4. The reference electrode 42 is a porous cermet electrode having a substantially rectangular shape in a plan view. An air introduction layer 48 constituted by porous alumina and connected to the reference gas inlet space is provided around the reference electrode 42, so that the reference gas (air) in the reference gas inlet space 43 is introduced to a surface of the reference electrode 42. In the first oxygen-partial-pressure detection sensor cell 60, an electromotive force V0 is caused between the inside pump electrode 22 and the reference electrode 42, by a difference in the oxygen concentration between the atmosphere of the first internal space 20 and the reference gas of the reference gas inlet space 43.

In the sensor element 101, the electromotive force V0 caused in the first oxygen-partial-pressure detection sensor cell 60 is used to feedback-control the variable power source 24 of the main pumping cell 21. Thereby, the pump voltage Vp0 applied to the main pumping cell 21 by the variable power source 24 can be controlled in accordance with oxygen partial pressure in the atmosphere of the first internal space 20. In the sensor element 101 according to the preferred embodiment, the pump voltage Vp0 applied to the main pumping cell 21 by the variable power source 24 is controlled such that the oxygen partial pressure in the atmosphere of the first internal space 20 can be set at a predetermined value that is low enough to allow an oxygen partial pressure control in the second internal space 40.

The third diffusion control part 30 applies a predetermined diffusion resistance to the measurement gas introduced from the first internal space 20 into the second internal space 40.

The second internal space 40 is provided as a space for performing a process concerning a measurement of a nitrogen oxide (NOx) concentration in the measurement gas introduced through the third diffusion control part 30.

In the second internal space 40, an auxiliary pumping cell 50 performs further adjustment of oxygen partial pressure on the measurement gas whose oxygen partial pressure has been adjusted in advance in the first internal space 20 and which has then been introduced through the third diffusion control part 30. This enables the NOx sensor 100 to measure a NOx concentration with a high accuracy.

The auxiliary pumping cell 50 is an auxiliary electrochemical pumping cell constituted by an auxiliary pump electrode 51, the outside pump electrode 23, and a part of the oxygen-ion conductive solid electrolyte interposed between these electrodes. The auxiliary pump electrode 51 is provided at a substantially entire part of the lower surface of the second solid electrolyte layer 6 facing the second internal space 40 and at a part of the spacer layer 5. Similarly to the inside pump electrode 22, the auxiliary pump electrode 51 is formed using a material having a weakened reduction ability with respect to the NO component in the measurement gas, or having no reduction ability with respect to the NO component in the measurement gas. That is, the auxiliary pump electrode 51 is also provided as a pump electrode having a low NO-reducing property, in which the reducing property with respect to the NO component is suppressed.

In the auxiliary pumping cell 50, a pump voltage Vp1 is applied by a variable power source 52 provided in the outside of the sensor element 101, to make a pump current Ip1 flow in a positive direction between the outside pump electrode 23 and the auxiliary pump electrode 51, and this allows oxygen existing within the second internal space 40 to be pumped out to the outside.

In the sensor element 101, a second oxygen-partial-pressure detection sensor cell 61 which is an electrochemical sensor cell is constituted by the auxiliary pump electrode 51, the reference electrode 42, and a part of the oxygen-ion conductive solid electrolyte interposed between these electrodes. In the second oxygen-partial-pressure detection sensor cell 61, an electromotive force V1 is caused between the auxiliary pump electrode 51 and the reference electrode 42, by a difference in the oxygen concentration between the atmosphere of the second internal space 40 and the reference gas (air) of the reference gas inlet space 43.

In the sensor element 101, the electromotive force V1 caused in the second oxygen-partial-pressure detection sensor cell 61 is used to feedback-control the variable power source 52 of the auxiliary pumping cell 50. Thereby, the pump voltage Vp1 applied to the auxiliary pumping cell 50 by the variable power source 52 can be controlled in accordance with oxygen partial pressure in the atmosphere of the second internal space 40. In the sensor element 101 according to the preferred embodiment, the pump voltage Vp1 applied to the auxiliary pumping cell 50 by the variable power source 52 is controlled such that the oxygen partial pressure in the atmosphere of the second internal space 40 can be set at a predetermined value that is low enough to have substantially no influence on the measurement of the NOx concentration.

The sensor element 101 further includes a measuring sensor cell 41 and a measuring pumping cell 47. The measuring sensor cell 41 is an electrochemical sensor cell constituted by a measuring electrode 44, the reference electrode 42, and a part of the oxygen-ion conductive solid electrolyte interposed between these electrodes. The measuring pumping cell 47 is an electrochemical pumping cell constituted by the outside pump electrode 23, the measuring electrode 44, and a part of the oxygen-ion conductive solid electrolyte interposed between these electrodes.

The measuring electrode 44 is a porous cermet electrode having a substantially rectangular shape in a plan view. The measuring electrode 44 is constituted by a porous cermet including zirconia and a metal capable of reducing NOx which is a measurement gas component. For example, as a metal component, Pt as a main component having Rh added thereto may be used. This makes the measuring electrode 44 function also as a NOx reducing catalyst for reducing NOx existing in the atmosphere of the second internal space 40.

The measuring electrode 44 is covered with an electrode protective layer 45. The electrode protective layer 45 is a porous alumina layer, and provided for limiting the amount of NOx flowing into the measuring electrode 44 to thereby allow the measuring electrode 44 to effectively maintain its catalytic activity. In other words, the electrode protective layer 45 applies a predetermined diffusion resistance to the measurement gas introduced into the measuring electrode 44.

In the measuring electrode 44, due to a catalytic activity effect thereof, NOx in the measurement gas is reduced or decomposed, to generate oxygen. As a result, in the measuring sensor cell 41, an electromotive force V2 is caused between the measuring electrode 44 and the reference electrode 42. A variable power source 46 of the measuring pumping cell 47 provided in the outside of the sensor element 101 is feedback-controlled based on the electromotive force V2, and thereby a pump voltage Vp2 applied to the measuring pumping cell 47 by the variable power source 46 can be controlled in accordance with oxygen partial pressure of oxygen generated in the measuring electrode 44. In the sensor element 101 according to the preferred embodiment, a current (NOx current) Ip2 flowing in the measuring pumping cell 47 at this time is detected, and a NOx concentration in the measurement gas is obtained based on the fact that the current Ip2 is substantially proportional to the NOx concentration in the measurement gas (the fact that the NOx current Ip2 and the NOx concentration are in a linear relationship).

Figure 2:
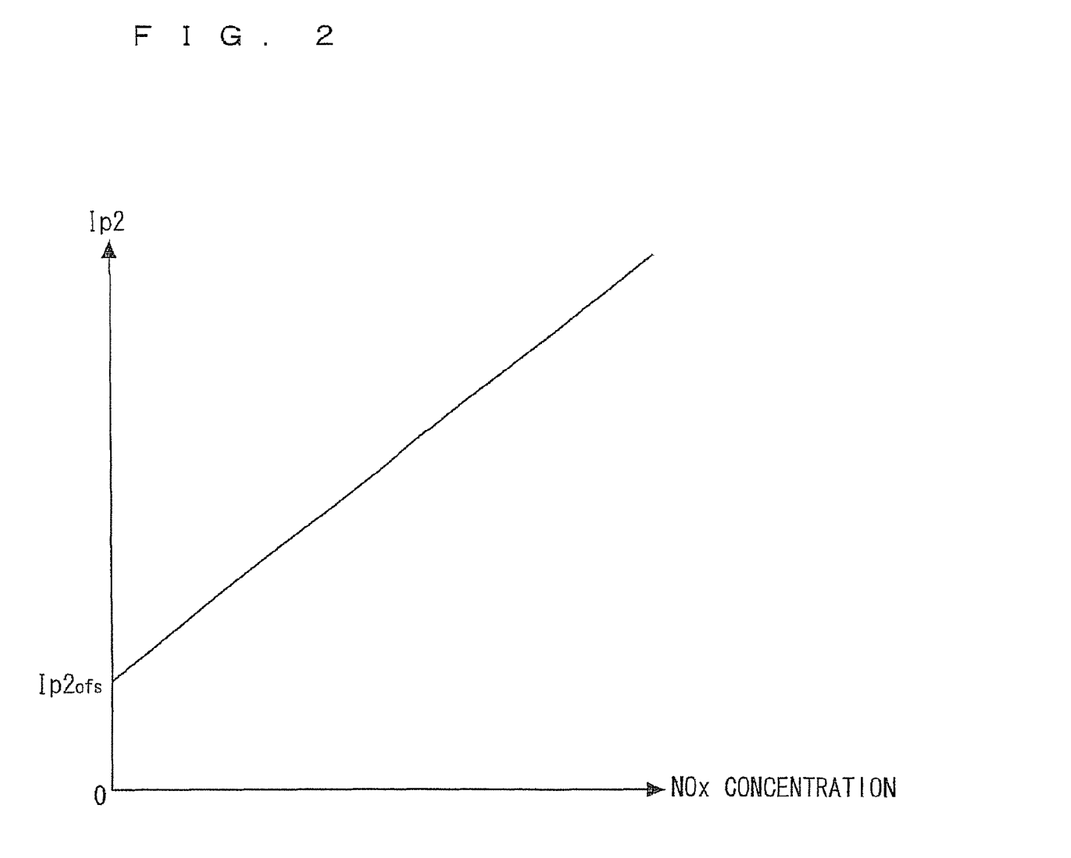
FIG. 2 illustrates a graph showing a functional relationship between a NOx current Ip2 and a NOx concentration.

FIG. 2 illustrates a graph (sensitivity characteristics) showing a functional relationship between the NOx current Ip2 and the NOx concentration. Ideally, the value of the current Ip2 should be 0 in a state where no NOx exists, but actually, oxygen is not completely removed from the measurement gas, and a small amount of the oxygen remains in the measurement gas having reached the measuring electrode. Therefore, even in the state where no NOx exists, a current flows due to oxygen ion generated by decomposition of the remaining oxygen. The NOx current Ip2 in this state where the NOx concentration is zero is particularly referred to as an offset current $Ip2_{ofs}$.

The sensitivity characteristics (specifically, the offset current $Ip2_{ofs}$ and the gradient of the graph) shown in FIG. 2 are identified for each individual sensor element 101 in advance prior to the use thereof. In an actual NOx detection, the value of the current Ip2 is constantly measured, and a NOx concentration corresponding to each measured value is obtained based on the previously identified sensitivity characteristics.

In the sensor element 101, by measuring an electromotive force $V_{ref}$ caused between the outside pump electrode 23 and the reference electrode 42, oxygen partial pressure in the outside of the sensor element 101 can also be recognized.

Moreover, in the sensor element 101, a heater 70 is formed so as to be interposed between the third substrate layer 3 and the second substrate layer 2 from above and below. The heater 70 generates heat by being fed power from the outside through a heater electrode (not shown) provided on a lower surface of the first substrate layer 1. Heat generation by the heater 70 enhances the oxygen-ion conductivity of the solid electrolyte constituting the sensor element 101. The heater 70 is buried over an entire area extending from the first internal space 20 to the second internal space 40, so that the heater 70 can heat and keep warm a predetermined position of the sensor element 101 at a predetermined temperature. A heater insulating layer 72 constituted by alumina or the like is formed on upper and lower surfaces of the heater 70, for the purpose of providing an electrical insulation between the second substrate layer 2 and the heater 70 and an electrical insulation between the third substrate layer 3 and the heater 70 (hereinafter, a set of the heater 70, the heater electrode, and the heater insulating layer 72 is also referred to as a heater part).

As described above, in the NOx sensor 100 according to the preferred embodiment, the main pumping cell 21 and the auxiliary pumping cell 50 are operated so that the measurement gas whose oxygen partial pressure is always maintained at a constant low value (the value having substantially no influence on the measurement of NOx) is given to the measuring electrode 44. The pump current, which flows in the measuring pumping cell 47 in accordance with the electromotive force caused in the measuring sensor cell 41 due to generation of oxygen resulting from NOx reduction or NOx decomposition in the measuring electrode 44, has a linear relationship with the NOx concentration in the measurement gas. Based on this fact, the NOx concentration in the measurement gas can be recognized.

<Method for Manufacturing Sensor Element>

Next, a process of manufacturing the sensor element 101 having the above-described structure will be described. In outline, in the preferred embodiment, predetermined patterns are formed on a plurality of green sheets containing, as a ceramic component, an oxygen-ion conductive solid electrolyte such as zirconia. Then, a laminated body of the green sheets is formed, and the laminated body is cut and baked, thus preparing the sensor element 101.

Hereinafter, a case where the sensor element 101 constituted by the six layers shown in FIG. 1 is prepared will be described as an example. In such a case, six green sheets corresponding to the first substrate layer 1, the second substrate layer 2, the third substrate layer 3, the first solid electrolyte layer 4, the spacer layer 5, and the second solid electrolyte layer 6 are prepared.

Figure 3:
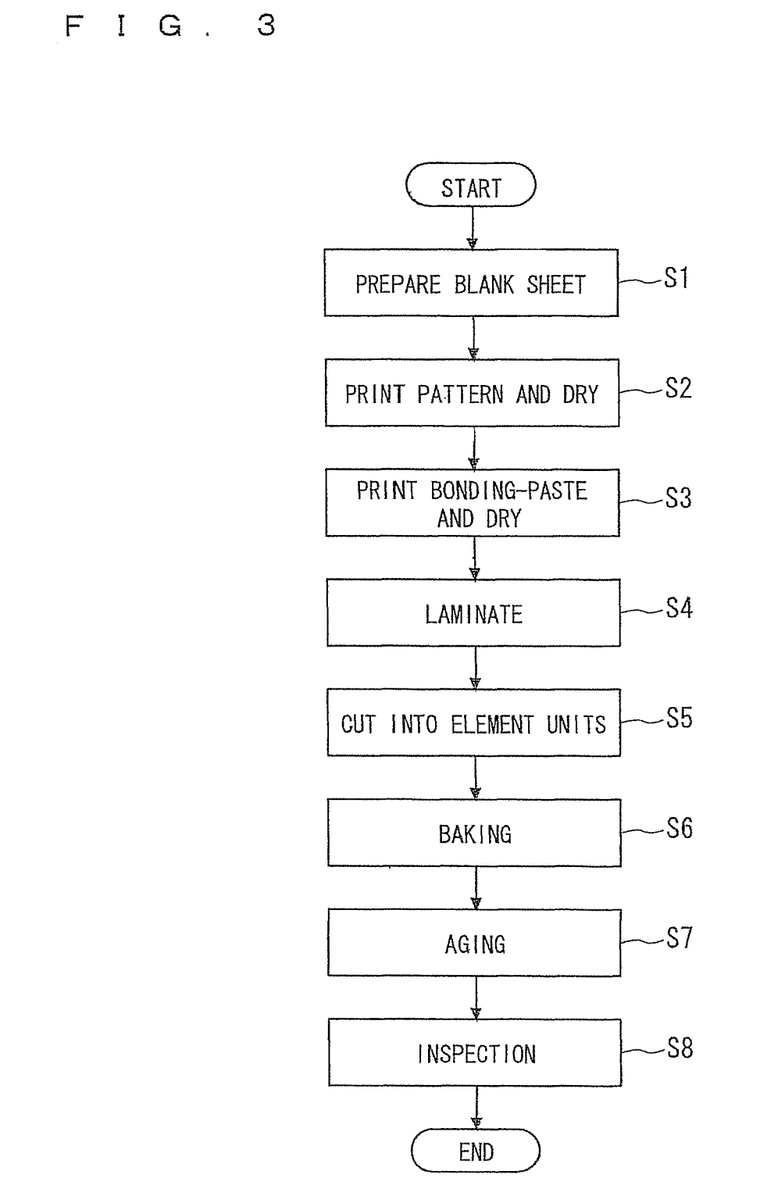
FIG. 3 shows a process flow for preparing the sensor element 101.

FIG. 3 shows a process flow for preparing the sensor element 101. To prepare the sensor element 101, firstly, a plurality of blank sheets (not shown) which are green sheets having no pattern formed thereon are prepared (step S1). The blank sheets have a plurality of sheet holes which are used for positioning in printing and laminating. The sheet holes are previously formed on a blank-sheet before forming a pattern through a punching process using a punching apparatus or the like. In a case of a green sheet which corresponds to a layer constituting an internal space, a penetrating portion corresponding to the internal space is also formed in advance through the same punching process or the like. Here, it is not always necessary that all the blank sheets corresponding to the respective layers of the sensor element 101 have the same thickness.

After the blank sheets corresponding to the respective layers are prepared, then a pattern printing and drying process is performed in which various patterns are formed on the respective blank sheets (step S2). To be specific, electrode patterns for the outside pump electrode 23, the inside pump electrode 22, the auxiliary pump electrode 51, the measuring electrode 44, and the reference electrode 42, etc., the electrode protective layer 45, the air introduction layer 48, an internal wiring (not shown), and the like, are formed. On a green sheet constituting the second solid electrolyte layer 6 which serves as the uppermost surface of the sensor element 101, a cut mark is printed which is used as a reference of a cutting position when the laminated body is cut in a subsequent step.

Printing of each pattern is performed by applying a pattern-forming paste, which is prepared in accordance with each required characteristics, to the blank sheet using a known screen-printing technique. For the drying process after the printing, known drying means may be used, too. In a preferred example, the drying process is performed in the air atmosphere at a temperature of 75° C. to 90° C., for example.

After the pattern printing is completed, then a printing and drying process of a bonding paste for laminating and bonding the green sheets corresponding to the respective layers to one another is performed (step S3). For the printing of the bonding paste, a known screen-printing technique may be used. For the drying process after the printing, known drying means may be used, too. It is also preferred that the drying process is performed in the air atmosphere at a temperature of 75° C. to 90° C., for example.

Subsequently, a pressure-bonding process is performed in which the green sheets having the bonding paste applied thereto are put in layers in a predetermined order and subjected to a predetermined temperature/pressure condition so that the green sheets are pressure-bonded to form a single laminated body (step S4). Specifically, the green sheets to be laminated are stacked and held onto a predetermined laminate jig (not shown) while being positioned with the sheet holes, and are heated and pressurized together with the laminate jig by a laminating machine such as a known oil-hydraulic press machine. In the heating and pressurization, the pressure, the temperature, and the time period depend on a laminating machine used. Appropriate conditions may be set such that a good lamination can be realized.

After the laminated body is obtained in the above-described manner, then the laminated body is cut at a plurality of portions thereof, so that a unit (referred to as an element body) for each individual sensor element 101 is cut out (step S5). The element body thus cut out is baked under a predetermined condition, and thereby evaporation of an organic component contained in the element body, sintering of the ceramic component, and additionally sintering of an electrode metal, and the like, make progress (step S6). In a preferred example, the baking is performed in the air atmosphere at a bake temperature of 1350° C. to 1400° C., for example.

An aging process (step S7) in a rich atmosphere is performed on the baked element body, for the purpose of reducing the electrode which has been oxidized in the baking. For forming the rich atmosphere, gas containing CO, $CH_4$, $C_2H_6$, $C_3H_8$, or the like, is used.

Then, various inspections such as inspection of external appearance and inspection of device characteristics are performed on the element body having gone through the aging process (step S8). If an element body passes all the inspections, the element body is, as the sensor element 101, stored in a predetermined housing and assembled into a main body (not shown) of the NOx sensor 100.

<Inspection of Device Characteristics>

Next, among the inspection steps included in the above-described process of manufacturing the sensor element 101, the inspection of device characteristics will be described. The inspection of device characteristics is inspection of electrical characteristics that is performed before the element body having gone through the aging process is assembled as the sensor element 101 into the main body of the NOx sensor 100. The inspection of device characteristics is performed in order to confirm that each of the pumping cells and the sensor cells has characteristics within a predetermined range that has been set as a standard. Hereinafter, for simplification of the description, the element body having gone through the aging process is simply referred to as the sensor element 101, irrespective of whether the element body has passed the inspection or not.

Figure 4:
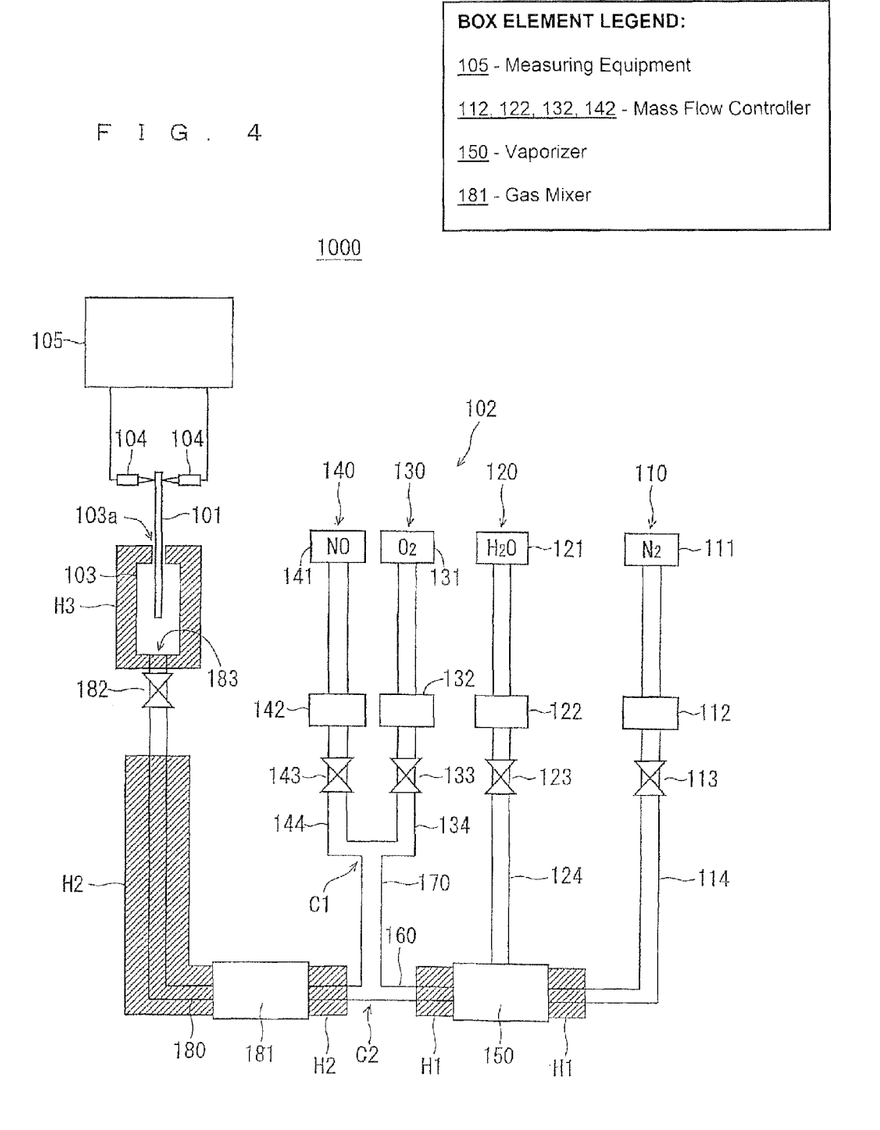
FIG. 4 is a schematic diagram illustrating an inspection equipment 1000 used for inspection of device characteristics.

FIG. 4 is a schematic diagram illustrating an inspection equipment 1000 used for the inspection of device characteristics. The inspection equipment 1000 includes a mixed gas feeder 102, a measurement chamber 103, and a measuring equipment 105. The mixed gas feeder 102 supplies a mixed gas mixed at a desired mixing ratio. The mixed gas is introduced from the mixed gas feeder 102 to the measurement chamber 103. The measuring equipment 105 can perform predetermined electrical measurement by connecting probes 104 to a predetermined position of the sensor element 101 placed in the measurement chamber 103. A measuring instrument or the like capable of measurement suitable for what is to be inspected may be appropriately used as the measuring equipment 105.

In the example shown in FIG. 4, for the sake of simplification, one measurement chamber 103 is connected to the mixed gas feeder 102. However, a supply pipe extending from the mixed gas feeder 102 may be branched so that a plurality of measurement chambers 103 are connected to one mixed gas feeder 102. In such a case, it is preferable that a plurality of sensor elements 101 can be measured concurrently.

In the example shown in FIG. 4, for the sake of simplification, the probes 104 are connected to the sensor element 101 in such a manner that an end portion of the sensor element 101 is sandwiched between the two probes 104. However, in an actual case, the number of probes 104 and how the probe 104 is connected are not limited thereto. A probe 104 for voltage application, a probe 104 for current passage, and additionally a probe 104 for current detection, which are properly prepared in accordance with a specific structure of the sensor element 101 and what is to be inspected in the inspection of device characteristics, are connected to appropriate positions (terminal positions (not shown) corresponding to the respective electrodes).

The mixed gas feeder 102 includes a nitrogen supply system 110, a water supply system 120, an oxygen supply system 130, and a NO supply system 140. These supply systems have a nitrogen supply source 111, a water supply source 121, an oxygen supply source 131, and a NO supply source 141, respectively, as supply sources (chemical cylinders, tanks, or the like) of respective substances. Mass flow controllers 112, 122, 132, and 142 for adjusting flow rates, and valves 113, 123, 133, and 143 are provided in the middle of the respective supply paths 114, 124, 134, and 144.

A supply path 114 of the nitrogen supply system 110 and a supply path 124 of the water supply system 120 are connected to a vaporizer 150. In the vaporizer 150, water supplied from the water supply system 120 is vaporized into water vapor which is then mixed with nitrogen supplied from the nitrogen supply system 110. A heater H1 capable of heating the atmosphere in the vaporizer 150 is attached to the vaporizer 150. The heater H1 is controlled by a temperature controller (not shown).

In the vaporizer 150, the water vapor and the nitrogen are mixed while the heater H1 is heating the atmosphere of the vaporizer 150 to approximately 100° C. to 120° C. This can suitably prevent the water from failing to be vaporized and thus remaining. A mixed gas of the water vapor and the nitrogen flows out of the vaporizer 150 into a first preliminary mixture path 160.

On the other hand, the oxygen supply system 130 and the NO supply system 140 meet at a junction C1, so that a mixed gas of the oxygen and the NO supplied from the oxygen supply system 130 and the NO supply system 140, respectively, flows in a second preliminary mixture path 170.

Furthermore, the second preliminary mixture path 170 meets the first preliminary mixture path 160 at a junction C2. Thereby, a mixed gas of the gases supplied from the first and second preliminary mixture paths 160 and 170, in other words, a mixed gas of all the gases supplied from the four supply systems, flows in a mixed gas supply path 180. In the mixed gas supply path 180, a gas mixer 181 is provided near the junction C2, so that the mixed gas having being sufficiently mixed by the gas mixer 181 is supplied to the measurement chamber 103 from a supply port 183 provided at an end of the mixed gas supply path 180. A valve 182 is provided in the mixed gas supply path 180, so that the valve 182 adjusts a flow rate of the mixed gas supplied to the measurement chamber 103.

Although in a preferred example, a so-called static mixer (static type mixer) is used as the gas mixer 181, a dynamic mixer may also be adoptable.

A heater H2 is attached to the mixed gas supply path 180. Preferably, a heater H3 is provided to the measurement chamber 103. The heater H2 and the heater H3 are controlled by a temperature controller (not shown). The heater H2 and the heater H3 maintain the temperature of the atmosphere of the measurement chamber 103, at approximately 100° C. to 120° C.

One end of the measurement chamber 103 is connected to the supply port 183 of the mixed gas feeder 102, and the other end thereof forms an opening 103$a$ communicating with the outside. Through the opening 103$a$, the sensor element 101 is inserted into the measurement chamber 103. In measurement of the measuring equipment 105, the sensor element 101 is positioned such that its side having the gas inlet 10 is inserted into the measurement chamber 103 and its side having terminal electrodes 151 and 152 protrudes out of the measurement chamber 103. Such a state is shown in FIG. 4.

In FIG. 4, a supply route extending from the nitrogen supply source 111 through the supply path 114 and the first preliminary mixture path 160 to the supply port 183 of the mixed gas supply path 180 has a squared C-like shape. This illustration is merely for the sake of convenience, and does not show an actual pipe layout of the mixed gas feeder 102.

In the preferred embodiment, in the inspection of device characteristics, a first mixed gas or a second mixed gas is supplied by the mixed gas feeder 102. The first mixed gas is a mixed gas containing: a nitrogen ($N_2$) gas as a first main component which occupies the maximum mixing ratio (flow rate ratio); an oxygen ($O_2$) gas as a second main component which occupies the next maximum mixing ratio of approximately 10% to 18%; and a water vapor ($H_2O$) as a minor component which occupies approximately several percent of the total. The second mixed gas is a mixed gas obtained by adding approximately several hundred ppm to 1000 ppm (for example, approximately 500 ppm) of nitrogen monoxide (NO) gas to the first mixed gas. In a preferred example, the first mixed gas contains 18% of the oxygen ($O_2$) gas and 3% of the water vapor ($H_2O$), with the remainder being the nitrogen ($N_2$) gas, and the second mixed gas contains 18% of the oxygen ($O_2$) gas, 3% of the water vapor ($H_2O$), and 500 ppm of the nitrogen monoxide (NO) gas, with the remainder being the nitrogen ($N_2$) gas. This second mixed gas is similar to an exhaust gas component of an exhaust gas from an internal combustion for which the NOx sensor 100 performs detection.

Figure 5:
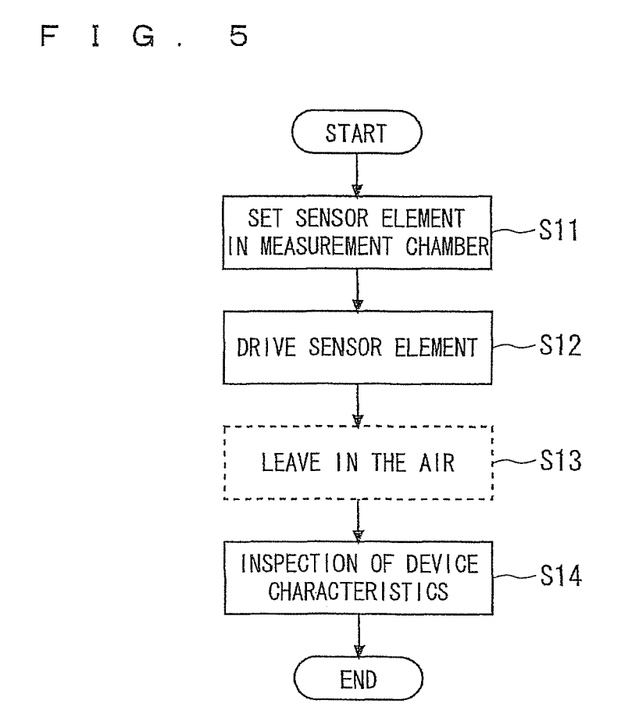
FIG. 5 shows a process flow concerning the inspection of the device characteristics.

FIG. 5 shows a process flow concerning the inspection of device characteristics in the preferred embodiment. As shown in FIG. 5, in the preferred embodiment, the sensor element 101 is set in the measurement chamber 103 (step S11), and then as a pre-process, the sensor element 101 is driven while the second mixed gas is being flown (step S12). Subsequently, while the first or second mixed gas atmosphere is being flown, the inspection of device characteristics is performed (step S14). Preferably, the inspection of device characteristics is performed not immediately after the pre-process is performed, but the inspection of device characteristics may be performed after the pre-processed sensor element 101 is left in the air for a predetermined time period (step S13). Here, driving the sensor element 101 means applying a predetermined voltage and passing a predetermined amount of current to each of the parts of the sensor element 101 including the heater part so as to make a state where, if the NOx current Ip2 is actually measured by the measuring probes 104, a current value corresponding to a NO concentration in the second mixed gas could be obtained.

It is preferable that a driving time period is approximately 10 minutes. Although the driving time period may be longer than 10 minutes, the driving is merely the pre-process for the inspection, and therefore extra driving is not preferable from the viewpoint of improvement of productivity.

This pre-process is performed for the purpose of stabilizing a state of each electrode included in the sensor element 101. To be specific, by performing the pre-process, the state of each electrode can be stabilized during the inspection of device characteristics and also during the actual use of the sensor element assembled in the main body of the NOx sensor 100.

Figure 6:
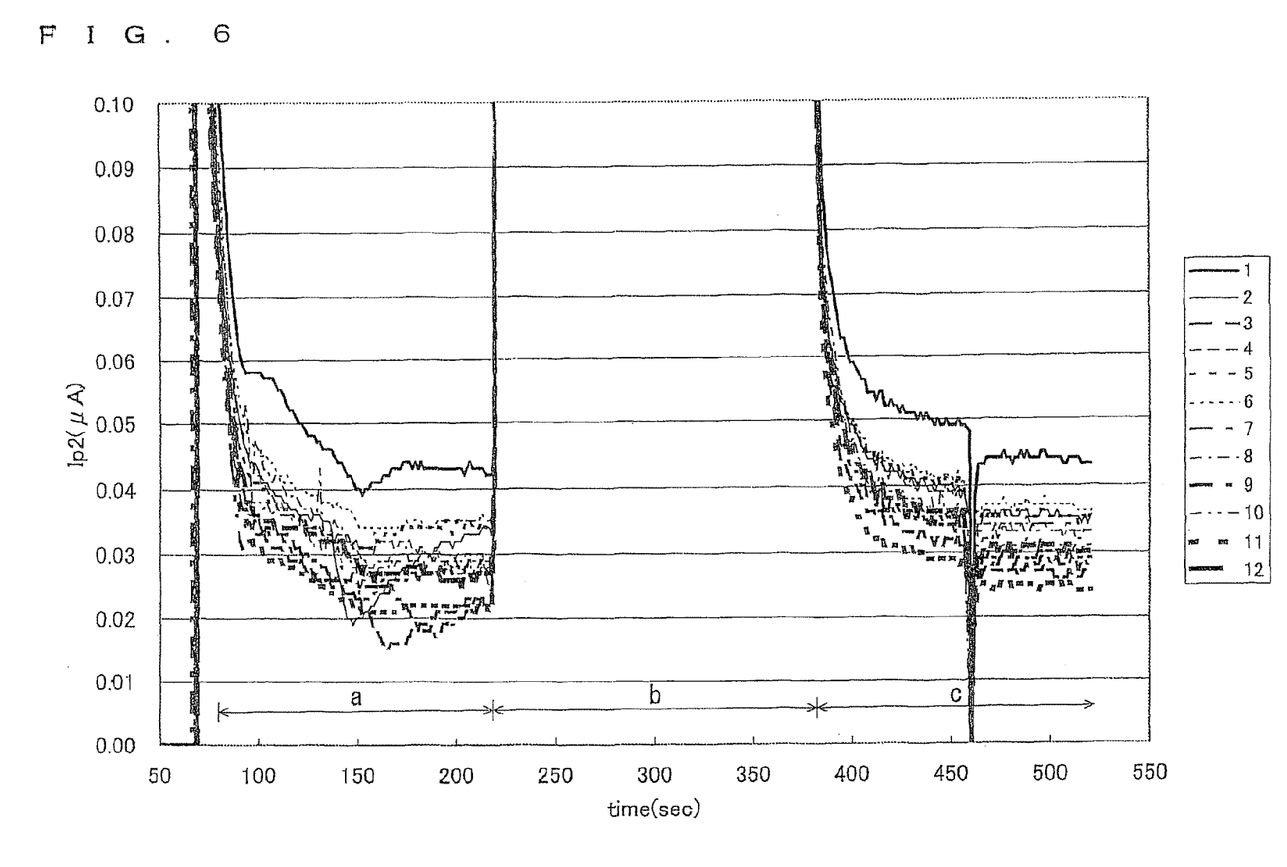
FIG. 6 illustrates the behavior of the NOx current Ip2 in a case where the inspection of the device characteristics is performed after driving of the sensor element 101 is performed as a pre-process.
Figure 7:
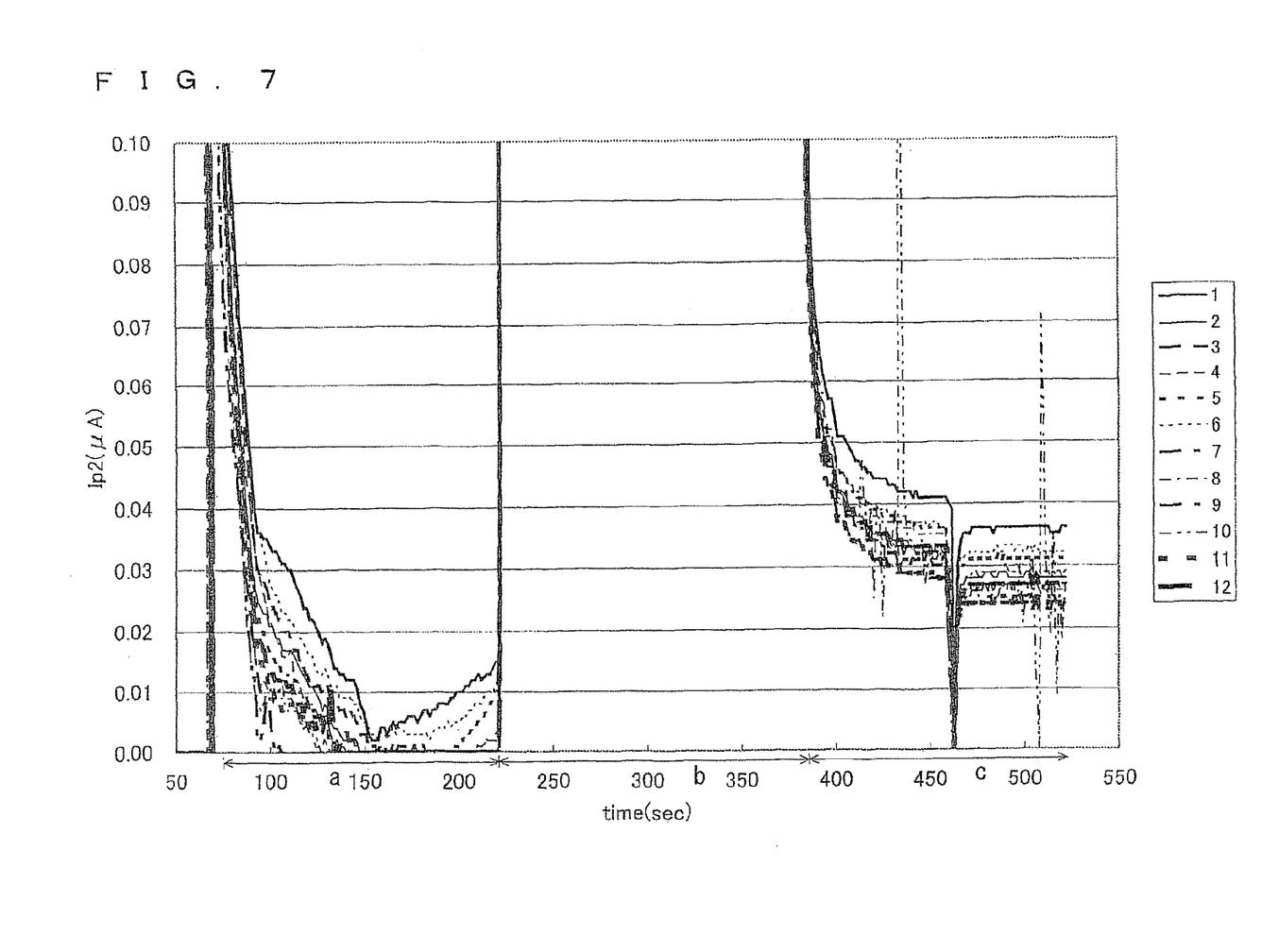
FIG. 7 illustrates the behavior of the NOx current Ip2 in a case where the inspection of the device characteristics is performed without performing the pre-process.

FIG. 6 illustrates the behavior of the NOx current Ip2 in a case where the inspection of the device characteristics is performed after driving of the sensor element 101 is performed as the pre-process. FIG. 7 illustrates, for comparison, the behavior of the NOx current Ip2 in a case where the inspection of the device characteristics is performed without performing the pre-process.

Both FIG. 6 and FIG. 7 show results obtained by observing, for each of twelve sensor elements 101, how the value of the NOx current Ip2 changed while the second mixed gas was intermittently supplied. Specifically, the results were obtained under the condition that the second mixed gas was flown only in a time period b and was not flown in time periods a and c which are before and after the time period b.

As described above, each of the electrodes of the sensor element 101 is formed by the baking which is performed in the course of manufacturing the sensor element 101. At that time, each of the electrodes is oxidized to some extent, and therefore the aging process is performed for reducing the oxidized electrodes. However, the degree of oxidation in the baking and the degree of reduction in the subsequent aging process vary among individual sensor elements. Even if the baking and the aging process are performed under the same condition, the degree of oxidation and the degree of reduction are not necessarily constant. Moreover, in the electrode after the aging process, a rich component such as CO, $CH_4$, $C_2H_6$, $C_3H_8$, or the like may be sometimes adsorbed and remain, and the degree thereof also varies among individual sensor elements 101 and individual electrodes.

When the inspection of device characteristics is performed without performing the pre-process, due to the above-described variation in the electrodes, the inspection progresses in an instable state where an oxygen pumping ability of the electrochemical pumping cell and a NOx reducing ability of the measuring electrode are not constant. FIG. 7 shows the results obtained in such a state. The value of the NOx current Ip2 in the time period a and the value of the NOx current Ip2 in the time period c are clearly different from each other, though they should be in the same range because the mixed gas is not flown. That is, there is no reproducibility of the value of the NOx current Ip2 in the state where no mixed gas is flown.

On the other hand, when the pre-process is performed as shown in FIG. 6, the value of the NOx current Ip2 in the time period a and the value of the NOx current Ip2 in the time period c are substantially in the same range. That is, there is reproducibility of the value of the NOx current Ip2 in the state where no mixed gas is flown. Here, in FIG. 6, the state where no mixed gas is flown occurs only twice, namely, in the time periods a and c. However, the inventors of the present invention have confirmed that when supply of the mixed gas and stopping thereof are subsequently repeated, the same reproducibility can be obtained, too.

This difference between the results shown in FIG. 6 and FIG. 7 indicates that performing the pre-process prior to the inspection of device characteristics is effective in stabilization of electrodes. If the inspection of device characteristics is performed even though electrodes are not yet stabilized, a sensor element 101 that would be determined to be a non-defective product under a stabilized state is actually determined to be a defective product. Therefore, performing the pre-process is effective in preventing such an erroneous decision.

If sensitivity characteristics are determined in a state where there is the variation as shown in FIG. 7, the sensitivity characteristics may not be reproduced during the subsequent use of the NOx sensor 100. Therefore, a NOx concentration calculated based on the sensitivity characteristics does not always have sufficient reliability. In a case where the pre-process is performed, the variation as shown in FIG. 7 is not seen, and therefore sensitivity characteristics having reliability can surely be determined.

It has been confirmed that, although the pre-process as shown in FIG. 7 is not performed on a sensor element 101, a state of electrodes is eventually stabilized if the sensor element 101 is driven for a long time in the course of the inspection of device characteristics. However, since a time period until such a stabilized state is obtained varies among individual sensor elements 101, this method is not suitable for the inspection of device characteristics which has to be performed in a routine in as short a time as possible.

Focusing only on the stabilization of electrodes, in principle, the object can also be accomplished by driving the gas sensor 100 after the sensor element 101 not subjected to the above-described pre-process is assembled in the main body of the gas sensor 100. However, this is not preferable because stability of the sensitivity characteristics is not necessarily ensured. Additionally, there is a problem of a higher risk that a sensor element 101 which is a defective product and therefore should be removed in an early stage may be allowed to reach an assembling step in a subsequent stage.

As described above, the inspection of device characteristics of the sensor element 101 is performed not immediately after the pre-process is performed, but it is preferable that the inspection of device characteristics may be performed after the pre-processed sensor element 101 is left in the air for a predetermined time period. In a case where the sensor element 101 has a defect such as a pinhole and oxygen enters the internal space through the defect, the value of the NOx current Ip2 of this sensor element 101 largely deviates from the standard. Since a sensor element 101 is left in the air before the inspection of device characteristics is performed, a sensor element 101 having such a defect can be easily determined to be a defective product during the inspection of device characteristics.

Here, leaving the sensor element 101 in the air for a predetermined time period does not mean that the sensor element 101 is in contact with the air in a very short time, but the sensor element 101 is left in a time period sufficient for oxygen to enter the sensor element 101 having a defect. To be specific, it is preferable that the time period for leaving is generally 30 minutes or more and 24 hours or less. Although the sensor element 101 may be left in a longer time period, the leaving is merely the pre-process for the inspection, and therefore extra leaving is not preferable from the viewpoint of improvement of productivity.

In this preferred embodiment, when the supply of the mixed gas from the mixed gas feeder 102 is stopped, the external air enters the measurement chamber 103 through the opening 103a of the measurement chamber 103. Therefore, a situation where the sensor element 101 is left in the air can be created merely by stopping the supply of the mixed gas while the sensor element 101 is left inserted into the measurement chamber 103 after the pre-process. That is, in the preferred embodiment, the pre-process on the sensor element 101, the leaving of the sensor element 101 in the air, and the inspection of device characteristics can be continuously performed by using the inspection equipment 1000. Thus, a series of steps for the inspection of device characteristics can be performed in an efficient manner.

As described above, in the preferred embodiment, the sensor element is driven for a predetermined time period before the inspection of device characteristics which is inspection of electrical characteristics of the sensor element is performed. Thereby, the inspection of device characteristics can be performed with the electrodes being in the stabilized state. This can prevent, in the inspection of device characteristics, occurrence of the erroneous decision which determines that a sensor element which should be determined to be a non-defective product is a defective product. Additionally, the sensitivity characteristics having reliability can be surely determined.

Thus, in the preferred embodiment, the yield of the product can be improved, and the NOx sensor having high reliability can be realized.

While the invention has been shown and described in detail, the foregoing description is in all aspects illustrative and not restrictive. It is therefore understood that numerous modifications and variations can be devised without departing from the scope of the invention.

What is claimed is:

1. A method for manufacturing a sensor element for a gas sensor, said sensor element comprising an electrochemical pumping cell and an electrochemical sensor cell, said method comprising the steps of:
   (a) printing and forming a wiring pattern of a conductive paste on a green sheet containing, as a main component, ceramic which is an oxygen-ion conductive solid electrolyte;
   (b) laminating a plurality of green sheets including the green sheet having been subjected to said step (a), and integrating said plurality of green sheets;
   (c) cutting out a plurality of element bodies from a laminated body obtained by said step (b);
   (d) baking the element body cut out by said step (c);
   (e) heating the element body having been subjected to said step (d), in a reducing atmosphere;
   (f) driving the element body having been subjected to said step (e), in an inspection-purpose gas atmosphere for a predetermined time period; and
   (g) after step (f), inspecting electrical characteristics of the element body having been subjected to said step (f),
   wherein, the element body having passed the inspection of said step (g) is assembled as said sensor element in a gas sensor.

2. The method according to claim 1, further comprising, between said step (f) and said step (g), the step of
   (h) leaving the element body having been subjected to said step (f), in the air,
   wherein the element body having been subjected to said step (h) is inspected in said step (g).

3. The method according to claim 2, wherein
   said step (g) includes the step of
   (g-1) inspecting whether or not each of said electrochemical pumping cell and said electrochemical sensor cell has electrical characteristics within a predetermined range that has been set as a standard.

4. The method according to claim 3, wherein
   in said step (g-1), electrical characteristics of said electrochemical pumping cell and electrical characteristics of said electrochemical sensor cell are evaluated in said inspection-purpose gas atmosphere.

5. The method according to claim 2, wherein
   said gas sensor is a NOx sensor.

6. The method according to claim 5, wherein
   in said step (f), said inspection-purpose gas atmosphere is an atmosphere of a gas containing a NOx gas and similar to a component of an exhaust gas from an internal combustion, and a predetermined voltage is applied and a predetermined amount of current is passed to each part of said sensor element for a predetermined time period,
   during said voltage application and current passage, said sensor element is in a state where a current value corresponding to a NOx concentration in the said inspection-purpose gas atmosphere is measurable.

7. The method according to claim 1, wherein
   said step (g) includes the step of
   (g-1) inspecting whether or not each of said electrochemical pumping cell and said electrochemical sensor cell has electrical characteristics within a predetermined range that has been set as a standard.

8. The method according to claim 7, wherein
in said step (g-1), electrical characteristics of said electrochemical pumping cell and electrical characteristics of said electrochemical sensor cell are evaluated in said inspection-purpose gas atmosphere.

9. The method according to claim 1, wherein
said gas sensor is a NOx sensor.

10. The method according to claim 9, wherein
in said step (f), said inspection-purpose gas atmosphere is an atmosphere of a gas containing a NOx gas and similar to a component of an exhaust gas from an internal combustion, and a predetermined voltage is applied and a predetermined amount of current is passed to each part of said sensor element for a predetermined time period,
during said voltage application and current passage, said sensor element is in a state where a current value corresponding to a NOx concentration in the said inspection-purpose gas atmosphere is measurable.

11. A method for inspecting electrical characteristics of a sensor element for a gas sensor, said method comprising the steps of:
(a) preparing a sensor element, said sensor element being an element body formed by baking a laminated body that includes a wiring pattern of a conductive paste and a plurality of green sheets containing, as a main component, ceramic which is an oxygen-ion conductive solid electrolyte, said sensor element having an electrochemical pumping cell and an electrochemical sensor cell;
(b) driving said sensor element in an inspection-purpose gas atmosphere for a predetermined time period; and
(c) inspecting electrical characteristics of the element body having been subjected to said step (b).

12. The method according to claim 11, further comprising, between said step (b) and said step (c), the step of
(d) leaving the element body having been subjected to said step (b), in the air,
wherein the element body having been subjected to said step (d) is inspected in said step (c).

13. A method for pre-processing a sensor element for a gas sensor which is performed prior to inspection of electrical characteristics, said method comprising the steps of:
(a) preparing a sensor element, said sensor element being an element body formed by baking a laminated body that includes a wiring pattern of a conductive paste and a plurality of green sheets containing, as a main component, ceramic which is an oxygen-ion conductive solid electrolyte, said sensor element having an electrochemical pumping cell and an electrochemical sensor cell; and
(b) driving said sensor element in an inspection-purpose gas atmosphere for a predetermined time period.

14. The method according to claim 13, further comprising the step of
(c) leaving the element body having been subjected to said step (b), in the air.

* * * * *